US007223895B2

(12) United States Patent
Sumner

(10) Patent No.: US 7,223,895 B2
(45) Date of Patent: May 29, 2007

(54) PRODUCTION OF PROPYLENE FROM STEAM CRACKING OF HYDROCARBONS, PARTICULARLY ETHANE

(75) Inventor: Charles Sumner, Livingston, NJ (US)

(73) Assignee: ABB Lummus Global Inc., Bloomfield, NJ (US)

( * ) Notice: Subject to any disclaimer, the term of this patent is extended or adjusted under 35 U.S.C. 154(b) by 86 days.

(21) Appl. No.: 10/716,232

(22) Filed: Nov. 18, 2003

(65) Prior Publication Data

US 2005/0107650 A1    May 19, 2005

(51) Int. Cl.
*C07C 6/02* (2006.01)
(52) U.S. Cl. .................. 585/329; 585/330; 585/324
(58) Field of Classification Search ............... 585/329, 585/330, 324
See application file for complete search history.

(56) References Cited

U.S. PATENT DOCUMENTS

| 4,458,096 A | | 7/1984 | Phillips et al. |
| 4,839,329 A | * | 6/1989 | Ihm et al. .................. 502/339 |
| 5,162,595 A | | 11/1992 | Wu et al. |

FOREIGN PATENT DOCUMENTS

EP    0 421 701 A    4/1991

OTHER PUBLICATIONS

Google Search for terms "distillation" and "relfux".*
PCT International Search Report for PCT/US2004/038213.
PCT Written Opinion of the International Searching Authority for PCT/US2004/038213.
Hydrocarbon Processing, Mar. 2003, pp. 70-126, XP-002322126.

* cited by examiner

*Primary Examiner*—Thuan Dinh Dang
(74) *Attorney, Agent, or Firm*—Alix, Yale & Ristas, LLP

(57) ABSTRACT

An ethane or other hydrocarbon feedstock is steam cracked to produce an ethylene stream which is processed in an ethylene plant recovery section to separate an ethane recycle and a polymer grade or chemical grade ethylene product stream. A portion of the ethylene product stream may then be reacted by dimerization to produce a butene stream. These formed butenes and/or butenes recovered from other sources and another portion of the ethylene product stream are reacted by metathesis to produce a propylene stream which is deethanized and separated from heavier hydrocarbons to produce the propylene product. The butene product stream may also be deethanized and is separated from heavier hydrocarbons. The overhead from the metathesis section deethanizer may be recycled to the ethylene plant recovery section. The reflux for the metathesis section deethanizer may be generated from the overhead or may be a portion of the ethylene product stream.

25 Claims, 6 Drawing Sheets

PRODUCTION OF PROPYLENE FROM STEAM CRACKING OF HYDROCARBONS, PARTICULARLY ETHANE

The present invention relates to a method of producing propylene from a hydrocarbon feed stream involving the steam cracking of the hydrocarbon and then processing the ethylene that is produced to produce the propylene. The invention is particularly applicable to a feed stream which is all or mostly ethane.

BACKGROUND OF THE INVENTION

Propylene has grown in importance and it now has the second highest worldwide production rate in the petrochemical industry. Propylene has a variety of downstream uses such as polypropylene and propylene oxide and the demand is expected to grow at rates of 5% to 6% each year. Therefore, new, lower-cost routes to propylene production are of high interest in the petrochemical marketplace. Today the majority of propylene is produced either as a principal byproduct in steam cracking units, which primarily produce ethylene, or as a byproduct from fluid catalytic cracking units, which primarily produce gasoline. Both the steam cracker and the fluid catalytic cracking unit require naphtha as a feedstock to make significant quantities of propylene product although lesser amounts of propylene can be produced by feeding propane or butane to the steam cracking unit. While gasoline demand remains strong, ethylene demand is expected to grow at an annual rate of only 3% to 4%, below the growth rate in propylene. In addition, much of the new steam cracker capacity will be based on using ethane as a feedstock. Using ethane as a feedstock to a steam cracker typically produces only ethylene as a final product. While hydrocarbons heavier than ethylene are present, typically the quantities are too small to warrant recovery and there is essentially no propylene produced. These two factors, the higher growth rate of propylene product demand and the reduced quantity of co-produced propylene from new steam cracker units, have and will manifest themselves in a shortage of the supply of propylene and higher propylene product values.

The primary reason many of the new steam cracking units are using ethane as a feedstock is because ethane is a co-product of natural gas production and has limited value for uses other than as a feedstock to a steam cracker unit. As natural gas demand and production rates grow for supplying electrical power and home heating needs, ethane availability increases beyond its regional demand. Since ethane cannot be readily or economically transported, regional demand is important and where its availability exceeds regional demand, its price is reduced. In many regions, ethane feed costs are 25% to 50% of other steam cracker feedstocks such as propane, butane or naphtha. This gives a large advantage to producing ethylene using low cost ethane feedstock. In addition, energy costs and capital investments for a steam cracker using ethane feedstock are far below the costs for using propane, butane or naphtha as a feedstock.

One commercial operation does produce polymer grade propylene by producing butene from polymer grade ethylene in a dimerization plant and then using the formed butene to react with additional polymer grade ethylene to form the polymer grade propylene in a metathesis plant. However, that operation uses a liquid feedstock which is cracked to produce both ethylene and propylene with the propylene production only being supplemented by the conversion of polymer grade ethylene to propylene. That operation does not involve the cracking of a fresh ethane feedstock to produce ethylene and then using the ethylene in metathesis and dimerization reactions as the only source of propylene. The ability to produce propylene using ethane feedstock is currently not practiced commercially.

The ability to effectively produce propylene using ethane, or mostly ethane, feedstock would significantly lower feedstock costs, energy costs and required capital investment just as it does for the production of ethylene. Providing a route for propylene production from ethane feedstock would also better utilize the available ethane feedstock. As noted above, the only current utilization for the ethane co-produced in natural gas production is to use it as a feedstock for ethylene production which raises concerns about an oversupply of ethylene product and the impact that would have on ethylene pricing and demand. Hence, some producers do not utilize all the available ethane. Providing a route to produce propylene from ethane feedstocks would help ensure that ethane utilization is high in all regions.

SUMMARY OF THE INVENTION

The object of the present invention is to provide an improved, more economical method for producing propylene from a hydrocarbon feedstock. The invention in its broadest form involves the steam cracking of the hydrocarbon feedstock to produce an ethylene-containing stream which is processed in an ethylene plant recovery section including a $C_2$ fractionator to obtain polymer and/or chemical grade ethylene and ethane for recycle. The ethylene is then reacted by metathesis with butene to produce propylene product. In one embodiment of the invention when the hydrocarbon feedstock is other than pure or mostly ethane, chemical grade ethylene is processed by metathesis to produce the propylene and the purge gases from the metathesis are processed in the ethylene plant recovery section, preferably in the $C_2$ fractionator.

In another embodiment of the invention, the hydrocarbon feedstock is either pure ethane or mostly ethane. In this embodiment, a portion of ethylene from the $C_2$ fractionator is processed by dimerization to produce butene and another portion of the ethylene is reacted by metathesis with that butene to produce the propylene product. The ethylene plant recovery section, the dimerization section and the metathesis section are all integrated for the handling of the purge and other process streams.

One embodiment disclosed herein is a method of producing propylene from ethane comprising the steps of (a.) steam cracking an ethane or primarily ethane feedstock thereby producing a cracking product containing ethylene hydrogen, ethane, methane, acetylene and $C_3$ and heavier hydrocarbons; (b.) treating the cracking product in an ethylene plant recovery section including removing the hydrogen, methane and $C_3$ and heavier hydrocarbons therefrom and converting the acetylene therein primarily to ethylene to thereby produce a treated cracking product containing primarily ethylene and ethane and including fractionating the treated cracking product in a $C_2$ fractionator and obtaining an ethylene fraction of chemical grade ethylene having an ethylene content of less than 99% by volume and a bottoms ethane fraction; (c.) recycling the bottoms ethane fraction to the steam cracking; (d.) reacting by dimerization in a dimerization section a first portion of the ethylene fraction thereby producing a butene-rich stream; (e.) reacting by metathesis in a metathesis section the butene in the butene-rich stream with a second portion of the ethylene fraction thereby producing a propylene-rich stream containing propylene, ethylene and ethane; (f.) separating propylene from the ethylene and ethane in the propylene-rich stream, and (g.) recycling at least a first portion of the ethylene and ethane from the propylene-rich stream to the $C_2$ fractionator.

Another preferred form of the invention is a method of producing propylene from a hydrocarbon feedatock comprising the steps of (a.) steam cracking the hydrocarbon feedstock thereby producing a cracking product containing ethylene, hydrogen, ethane, methane, acetylene and $C_3$ and heavier hydrocarbons; (b.) treating the cracking product in an ethylene plant recovery section including removing the hydrogen, methane and $C_3$ and heavier hydrocarbons therefrom and converting the acetylene therein to ethylene to thereby produce a treated cracking product containing primarily ethylene and ethane and including fractionating the treated cracking product in a $C_2$ fractionator and obtaining a chemical grade ethylene fraction having an ethylene content less than 99% by volume and a bottoms ethane fraction; (c.) recycling the bottoms ethane fraction to the steam cracking; (d.) reacting the chemical grade ethylene fraction by metathesis in a metathesis section with butene thereby producing a propylene-rich stream containing ethylene and ethane; (e.) removing the ethylene and ethane from the propylene-rich stream in a metathesis section deethanizer; and (f.) recycling at least a first portion of the removed ethylene and ethane to the $C_2$ fractionator.

Yet another embodiment is a method of producing propylene from ethane comprising the steps of (a.) steam cracking an ethane or primarily ethane feedstock thereby producing a cracking product containing ethylene, hydrogen, ethane, methane, acetylene and $C_3$ and heavier hydrocarbons; (b.)treating the cracking product in an ethylene plant recovery section including removing the hydrogen, methane and $C_3$ and heavier hydrocarbons therefrom and converting the acetylene therein primarily to ethylene to thereby produce a treated cracking product containing primarily ethylene and ethane and including fractionating the treated cracking product in a $C_2$ fractionator and obtaining a chemical grade ethylene fraction having an ethylene content of less than 99% by volume, a polymer grade ethylene fraction having an ethylene content of at least 99.5% by volume, and a bottoms ethane fraction; (c.) recycling the bottoms ethane fraction to the steam cracking; (d.) reacting by dimerization in a dimerization section a first portion of the chemical grade ethylene fraction thereby producing a butene-rich stream; (e.) reacting by metathesis in a metathesis section the butene in the butene-rich stream with a second portion of the chemical grade ethylene fraction thereby producing a propylene-rich stream containing propylene, ethylene and ethane; (f.) separating propylene from the ethylene and ethane in the propylene-rich stream, and (g.) recycling at least a portion of the ethylene and ethane from the propylene-rich stream to the $C_2$ fractionator.

DETAILED DESCRIPTION OF THE INVENTION

Figure 1:
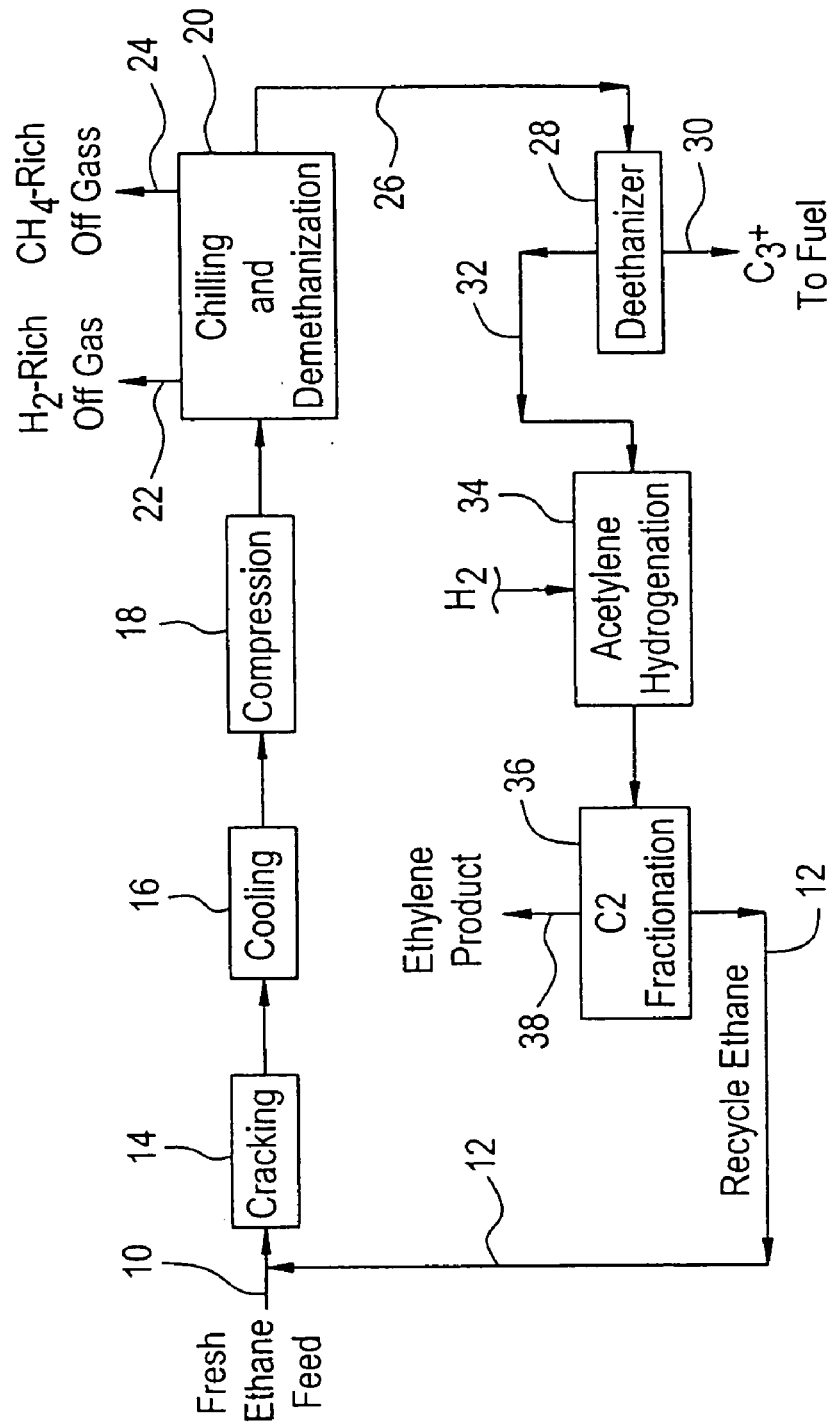
FIG. 1 is a process flow scheme showing a conventional prior art process involving the steam cracking of ethane to produce an ethylene product.

The production of ethylene from ethane feedstock in a steam cracking unit is widely practiced. FIG. 1 illustrates such a conventional steam cracker process using ethane as the sole feedstock. The fresh ethane feed 10, typically obtained by separation from natural gas, and a recycle ethane stream 12 are fed to a cracking heater 14 where, in the presence of steam, the ethane is heated with the resulting formation of ethylene and hydrogen as primary products and the formation of methane, $C_3$ and heavier hydrocarbons as secondary products. Ethane once-through conversion varies between 50 and 80%, with most commercial plants operating in the 60–75% conversion region. The steam cracker effluent is then treated in the ethylene plant recovery section where it is first cooled at 16 and then compressed at 18. At 20 the compressed stream is then chilled to separate hydrocarbon condensates from light gases 22 such as hydrogen and CO and the hydrocarbon condensates are demethanized to separate out methane 24. The demethanizer bottoms 26 flow to a deethanizer 28 where $C_3$ and heavier hydrocarbons are separated in the bottoms 30 and $C_2$ hydrocarbons are recovered the overhead 32. The deethanizer overhead 32 is then selectively hydrogenated at 34 to convert acetylene to ethylene after which the $C_2$ mixture flows to a $C_2$ fractionator 36.

In the $C_2$ fractionator 36, polymer-grade ethylene is typically taken as the overhead product 38 and an ethane rich stream 12 is taken as the bottom product. The ethane rich bottom product 12 is recycled back to the cracking heaters 14. The polymer grade ethylene can be taken as a direct overhead product or, alternately, it could be withdrawn as a side product a few separation stages down from the top of a fractionation tower, with the top trays then functioning as a pasteurization section to concentrate light gases such as hydrogen and methane in a small vent gas stream taken overhead.

In most of these prior art ethane crackers, the $C_3$ and heavier hydrocarbons are not recovered as chemical products but rather utilized as fuel products. This is because the quantity of these compounds is low in a pure ethane cracker. In a very large ethane cracking plant, or in an ethane cracking plant which also cracks propane, then it may be economical to recover propylene, and perhaps, also other heavier products for chemical use. But typically, the recovered non-fuel products heavier than ethylene are still made in low quantities.

In one embodiment of the present invention, a steam cracker for ethane or primarily ethane (defined as 70% or more ethane) is designed to produce ethylene. The ethylene is recovered and some is dimerized to butene. Then the produced butene is reacted with additional ethylene recovered from the steam cracker to produce propylene. Thus, an ethane cracker based complex can produce both ethylene and propylene products. Within the context of the overall process flow schemes, several process integrations are possible to improve economics.

Figure 2:
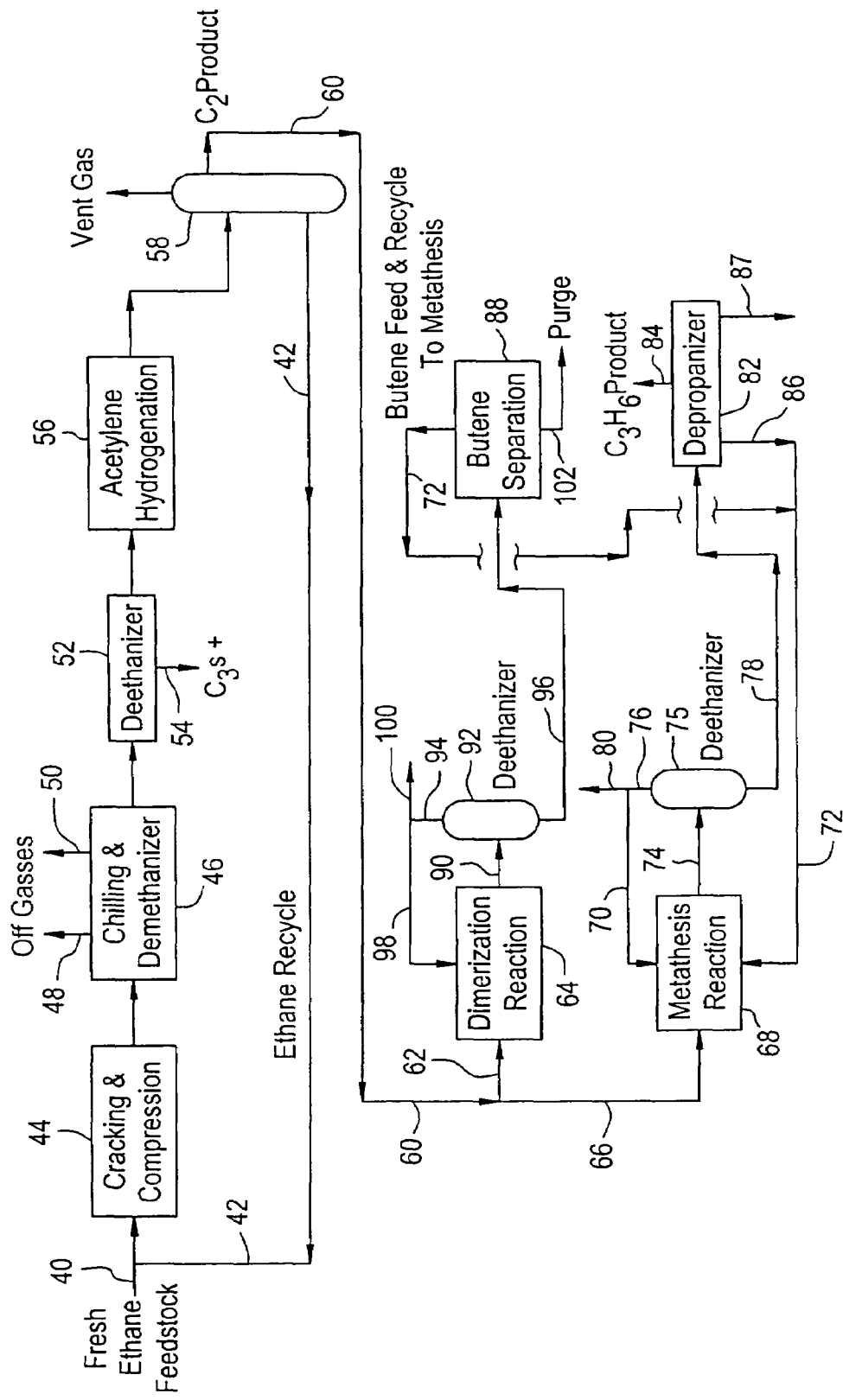
FIG. 2 is a process flow scheme illustrating one embodiment of the present invention involving the steam cracking of ethane to produce a propylene product.

FIG. 2 illustrates a first embodiment of the invention wherein the fresh ethane or primarily ethane feed 40 and the recycle ethane stream 42 are cracked, cooled and compressed at 44. The compressed stream containing the ethylene, hydrogen, methane and $C_3$ and heavier hydrocarbons, just as in the prior art illustrated in FIG. 1, is then chilled and demethanized at 46 removing light gases 48 and methane 50. The demethanizer bottoms are then deethanized at 52 where the $C_3$ and heavier hydrocarbons 54 are separated. The deethanizer overhead is then selectively hydrogenated at 56 to convert the acetylene primarily to ethylene. The $C_2$ mixture is then fractionated at 58 to separate the ethane recycle 42 and the ethylene product 60. Although not shown, the $C_2$ fractionator 58 would have a typical reboiler and overhead condenser and separator to produce reflux. The demethanizer 46, deethanizer 52 and the $C_2$ fractionator 58 are referred to as the ethylene plant recovery section. As an option for this ethylene plant recovery section, the deethanizer may be first, followed by the acetylene hydrogenation unit and then followed by the demethanizer. The demethanizer bottoms would then flow to the $C_2$ fractionator 58. The ethylene product 60 is then split with a portion 62 going to the dimerization reaction 64 and the other portion 66 going to the metathesis reaction 68.

The ability to produce propylene, by reacting butene and ethylene is something that, while not widely practiced commercially, is known to the industry. This process route utilizes a chemistry called olefins metathesis. Fresh ethylene 66 and recycled ethylene 70 and butenes 72, from the dimerization reaction 64 to be described, flow to the metathesis reactor 68 where they react to form an equilibrium mixture of propylene, ethylene and butenes, as well as small quantities of $C_5$ and heavier olefins. Ethylene conversion is typically below 50% per pass. The metathesis reaction including the temperatures, pressures and catalysts are well known in the art. The reactor effluent 74 flows to a deethanizer 75 wherein $C_2$'s are taken overhead at 76 and the $C_3$ and heavier hydrocarbons are in the bottoms product. Most of the $C_2$'s form the recycle 70 back to the reactor 68. A small purge 80 is taken to limit the buildup of inerts, chiefly ethane. The deethanizer bottoms 78 flows to a depropanizer 82 where the final polymer-grade propylene is distilled overhead at 84. Two bottoms products are usually taken. One is a side-stream 86 containing mostly butenes which is recycled back to the metathesis reactor 68. A bottoms stream 87 is also taken as a purge to limit the buildup of inerts, chiefly n-butane, and also to reject the $C_5$'s and heavier products formed in the reactor.

The ability to produce butene, either butane-1 or butene-2, by reacting ethylene with itself is also known to the industry and is called dimerization. Dimerization of ethylene to preferentially produce butene-2 is practiced commercially and is used in the present invention as a source of the feedstock for metathesis. The conversion of the ethylene is less than 100% and typically about 80% or greater. The effluent 90 from the dimerization reactor 64 flows to the deethanizer 92 wherein unreacted ethylene and ethane in the overhead 94 are separated from the butene in the bottoms 96. The overhead 94 is mostly recycled at 98 back to the reactor 64 and a small purge 100 is withdrawn to again control the buildup of inerts, chiefly ethane. The deethanizer bottoms 96 flows to a butene separation 88 where the product butane 72 and a purge stream 102 are withdrawn. The product 72 then goes to the metathesis reaction 68 for the production of the propylene. The purges 80 and 100 from the deethanizers 75 and 92 can be recycled back to the recovery section of the ethylene plant, i.e., back to the deethanizer 46 or deethanizer 52 or preferably to the $C_2$ fractionator 58. Alternately, they can be recycled back to the charge gas compressor, although this is less preferable.

Figure 3:
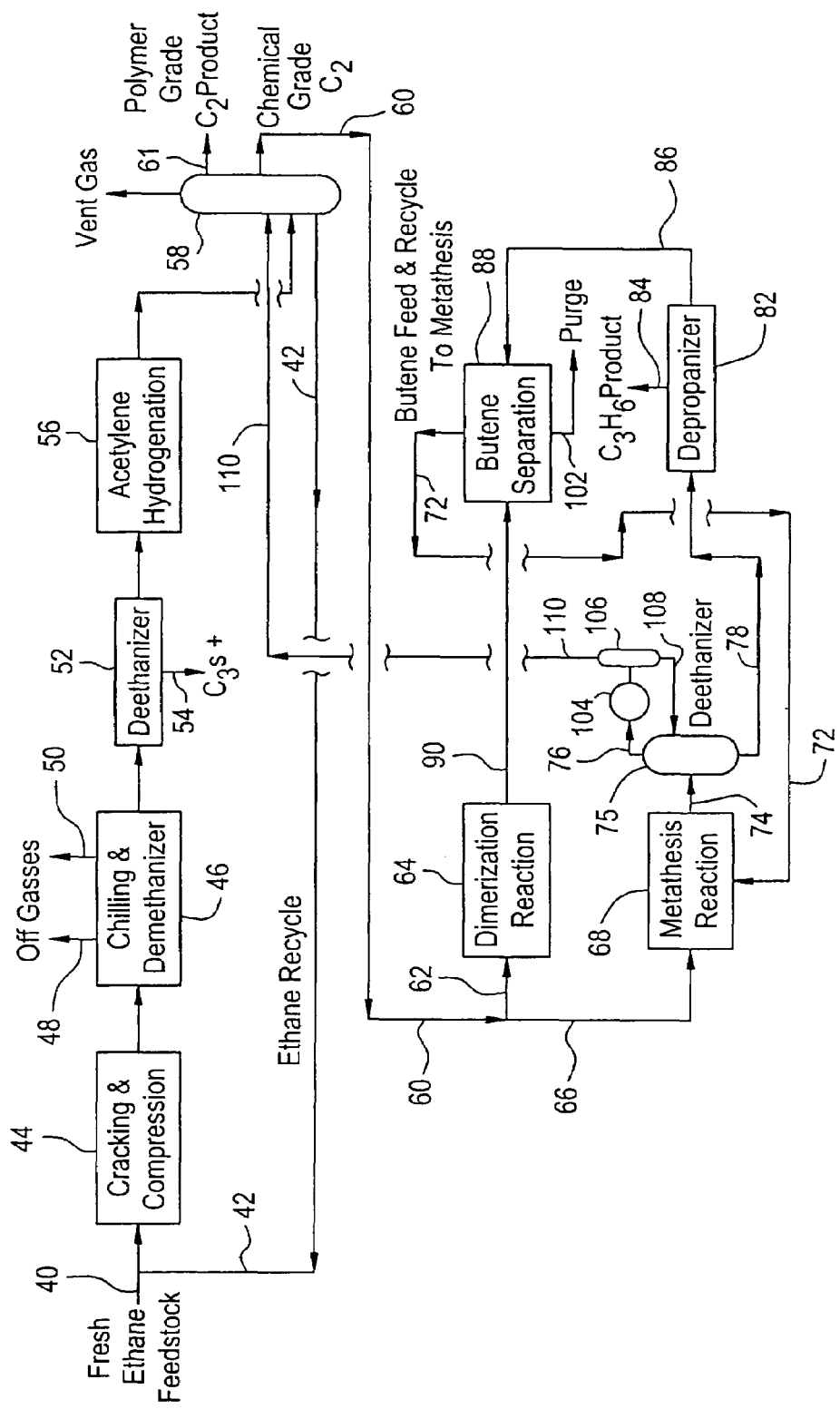
FIG. 3 is a process flow scheme similar to FIG. 2 but illustrating a variation of the process.

FIG. 3 illustrates another embodiment of the invention which uses a lower purity, chemical grade ethylene for dimerization and metathesis. Polymer grade ethylene has a purity usually above 99%, typically 99.5% plus, or more typically, 99.9% plus, whereas this embodiment of the invention uses chemical grade ethylene which is less than 99% pure and typically from 90 to 95% pure with the balance being essentially ethane. The chemical grade ethylene product 60 is now withdrawn as a side stream from a lower tray in the $C_2$ fractionator 58. Polymer-grade ethylene stream 61 may also be withdrawn as a source of ethylene for polymer production.

The advantage of using lower purity ethylene is a reduction in the capital cost and the operating cost of the ethylene plant complex. The separation of ethylene and ethane is capital and energy-intensive. It is more economical to produce a lower purity, chemical grade ethylene product and then convert some of this contained ethylene to butenes in the dimerization section and to propylene in the metathesis section. The resulting ethylene-ethane mixture is then upgraded to a chemical-grade purity.

In this FIG. 3 embodiment, there is an integration between the dimerization, metathesis and ethylene plant sections. The lower purity, chemical grade ethylene is utilized for both the dimerization and metathesis reactions. Unconverted ethylene and contained ethane from both of these reactions are recycled, directly or indirectly, back to the recovery section of the ethylene plant, preferably back to the $C_2$ fractionator or less preferably to the deethanizer or demethanizer.

The butene product 90 from the dimerization reaction 64 containing the unreacted ethylene and the contained ethane is fed directly to the butene separation 88 rather than to a deethanizer as in FIG. 2. Unconverted $C_2$'s are recovered in the butene separator overhead by being co-absorbed in the fresh and recycle $C_4$'s to the metathesis reactor, eliminating the need for the deethanizer 92 as in FIG. 2. The depropanizer, 82, would produce a propylene product, 84, as in FIG. 2 and a single bottom product, 86. The bottom product from the depropanizer 82, containing mostly butenes as well as other butane and heavier hydrocarbons, is then fed to the butene separation 88. The purge stream 102 is removed and the combined product butene 72 is fed to the metathesis reaction 68. The propylene-containing metathesis effluent 74 flows to the deethanizer 75 where the remaining $C_2$'s from both the dimerization and metathesis reactions are removed in the overhead 76. The overhead is cooled and partially condensed at 104 and separated at 106 to provide the reflux 108.

The net overhead 110 is preferably returned to the $C_2$ fractionator 58. The net overhead 110 enters the $C_2$ fractionator 58 at a stage that is not necessarily the same as the feed from the steam cracking plant, allowing for more efficient operation of this tower. The recycle ethylene flow back to the reactor is then the same purity as the chemical grade ethylene product. No buildup of ethane occurs, leading to a higher partial pressure of ethylene in the reactors, at a constant reactor operating pressure. No separate purge of inerts from the reactor loops is required. Rather, the inerts are purged as essentially pure ethane from the bottom of the $C_2$ fractionator, limiting the losses of ethylene. The use of this process feature could also result in a lower metathesis reactor operating pressure. The reflux ratio and stripping section heat input for the deethanizer 75 are reduced if the $C_2$ separation tower can be operated at lower pressure. Refrigeration is required but this can be provided by the refrigeration system present in the ethylene plant in a separate overhead condenser at an appropriate tower pressure and refrigeration temperature level.

Figure 4:
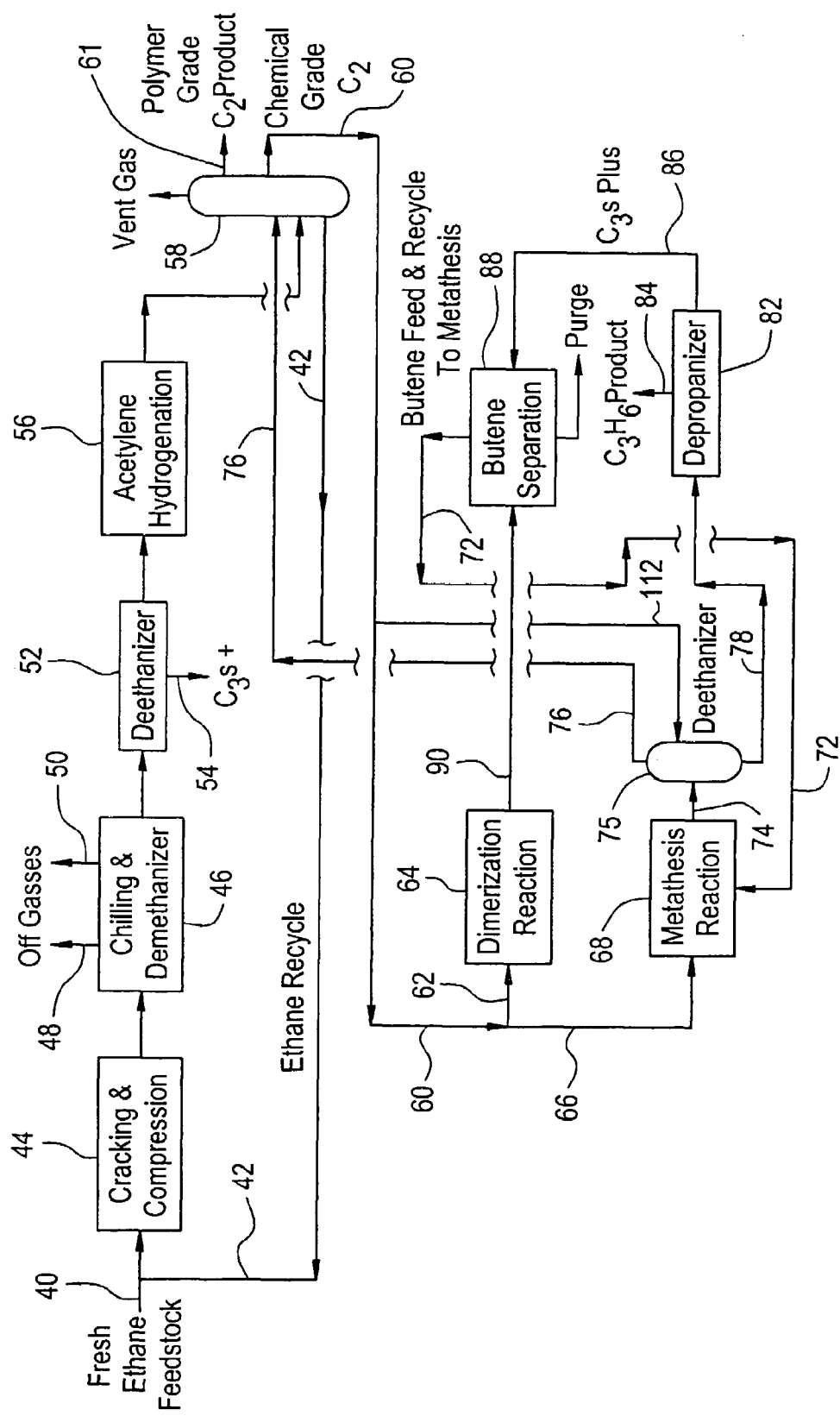
FIG. 4 is a process flow scheme illustrating a further variation of the invention.

Alternately, especially when using chemical grade ethylene, the deethanizer 75 may be fully integrated with the ethylene fractionator 58 and operated at the same pressure. No separate condenser, separator drum or reflux pumps are needed. This is shown in FIG. 4 which is a total integration rather than the partial integration as introduced in FIG. 3. In this concept, the deethanizer in the metathesis unit does not have an overhead system to produce reflux. Rather, the total overhead of this tower system flows directly to the $C_2$ fractionator. The chemical grade product from the $C_2$ fractionator then provides both the fresh feed and the recycle to the metathesis reactors and also provides the reflux to separate the $C_2$ stream from heavier streams in the metathesis section deethanizer. Clearly, there will be fewer pieces of process equipment required for the FIG. 4 process scheme versus FIG. 3. The total energy consumption and the total capital cost of the two process schemes will depend upon the specifics of the process, as practiced in a particular design. Both process schemes, however, are a clear improvement over the prior art, utilizing polymer grade ethylene and with no direct integration with the ethylene fractionator. In prior art metathesis plants, the deethanizer has operated at approximately 400 psi, with cooling of the overhead provided by propylene refrigeration, typically operating at approximately −20° F. to +10° F. level. In the FIG. 4 embodiment of the invention, this deethanizer 75 can be operated at the same pressure as the $C_2$ fractionator 58. The total overhead vapor 76 flows to the $C_2$ fractionator. Reflux 112 to the deethanizer is a portion of the total chemical grade ethylene 60 from the $C_2$ fractionator.

The main commercial markets for this integrated process are believed to be ethane steam cracking to make polymer-grade ethylene and polymer grade propylene products. However, the integrations between the ethylene fractionator and the metathesis plants are applicable to olefin plants, irrespective of feedstock utilized. Two integration concepts between the steam cracker, the ethylene plant recovery section and the dimerization and metathesis section deethanizers are taught and both of these inventive concepts are applicable to the integration of ethylene plants and metathesis plants whatever the feedstock to the steam cracker and whatever the process configuration of the steam cracker.

If there is a substantial amount of cracking of propane and heavier, it is possible, and practiced commercially, to have the depropanizer as the first hydrocarbon removal tower. Often the acetylene hydrogenation unit is located on the overhead of the depropanizer when this process configuration is utilized. The depropanizer overhead would then flow to either a demethanizer or deethanizer. If the second hydrocarbon removal tower is a demethanizer, then the demethanizer bottoms would flow to a deethanizer and the deethanizer overhead would flow to a $C_2$ fractionator. The concepts of the present invention would also apply to this process configuration. Similarly, the depropanizer overhead could flow to a deethanizer, then the deethanizer overhead to a demethanizer. The demethanizer bottoms would then flow to a $C_2$ fractionator. The concepts of the present invention would also apply to this process configuration.

The invention, in either the partial or total integration modes, enables the dimerization and metathesis units to operate at relatively high concentration of ethylene in their reaction loops while only providing chemical-grade purity ethylene rather than polymer-grade purity ethylene. In the total integration mode, it also enables deethanization in the metathesis plant to be carried out at a much lower pressure and potentially with fewer equipment items. In the metathesis area, this lower pressure deethanization further enables the metathesis reaction itself to proceed at a lower pressure, decreasing equipment costs.

In the invention as depicted in FIGS. 3 and 4, no direct recycle from the deethanizer 75 in the metathesis section to the metathesis reactor 68 is practiced. Unconverted ethylene is processed in the ethylene plant ethylene fractionator 58 and chemical-grade ethylene is recycled to the reactors. In practice, for the FIG. 3 embodiment, it is possible to send some of the unconverted ethylene recovered from the overhead of the metathesis plant deethanizer 75 to the metathesis and dimerization reactors and the balance of the ethylene recycle sent to processing in the $C_2$ fractionator 58.

The drawings show an ethylene fractionator 58 which would have a pasteurization section above the main rectification section and all products are produced as side streams. It is also possible to utilize a secondary demethanizer instead of a pasteurization section to separate lights. In this operation, the overhead of the ethylene fractionator, as a liquid, flows to the secondary demethanizer, which is typically a stripping column. Light gases plus associated ethylene are withdrawn overhead and the bottoms is the polymer-grade ethylene product. The overhead can be recycled back to a low pressure demethanizer for recovery of $C_2$'s or alternately, to the charge gas compressor of the ethylene plant.

In a plant with a front end deethanizer or front end depropanizer, neither a pasteurization section or secondary demethanizer may be required. The partial or total integration concepts between the $C_2$ fractionator and the dimerization and metathesis sections would still apply, however. The invention, with minor detail changes, is thus applicable whatever the fundamental process flow configuration of the steam cracker might be and is also applicable whatever cracking feedstock might be utilized.

The combination of processing steps of the present invention provides a unique route to propylene production from ethane or primarily ethane feedstocks. This route is a much lower cost production route for propylene (1) because of the use of lower cost ethane feedstocks relative to the propane, butane, naphtha or gas oil feedstocks used in steam cracking units or the heavy oil feedstocks used in fluidized catalytic cracking units; (2) because it consumes less energy than propylene production from steam crackers; and (3) because it has a lower capital investment, for a given polymer grade propylene production than either heavy feed steam crackers or fluidized catalytic cracking units. It also produces lower greenhouse gas emissions and therefore is a more environmentally friendly route.

The use of chemical grade ethylene from a steam cracker and using metathesis and dimerization have been discussed above. These concepts are also applicable to steam-cracking plants operated with any hydrocarbon feedstock. For example, it is possible with a mixed ethane/propane feedstock with less than 70% ethane or even a propane feedstock to utilize both dimerization and metathesis to increase propylene production. For butane and heavier hydrocarbon feeds to the steam cracker, and for most steam crackers which utilize propane feedstock, economics favor the use of by-product cracked $C_4$'s to be the source of butenes for metathesis. Thus, these plants will not need an ethylene dimerization section. Only the steam cracking plant with the ethylene plant recovery section and the metathesis section will be required. The recovery of butene from cracked $C_4$ streams and other process steps available to produce butene suitable as the source of the butene for the metathesis are well known to those skilled in the art. The integration steps taught in FIGS. 3 and 4, however, are novel and can be utilized for this plant configuration as well.

Figure 5:
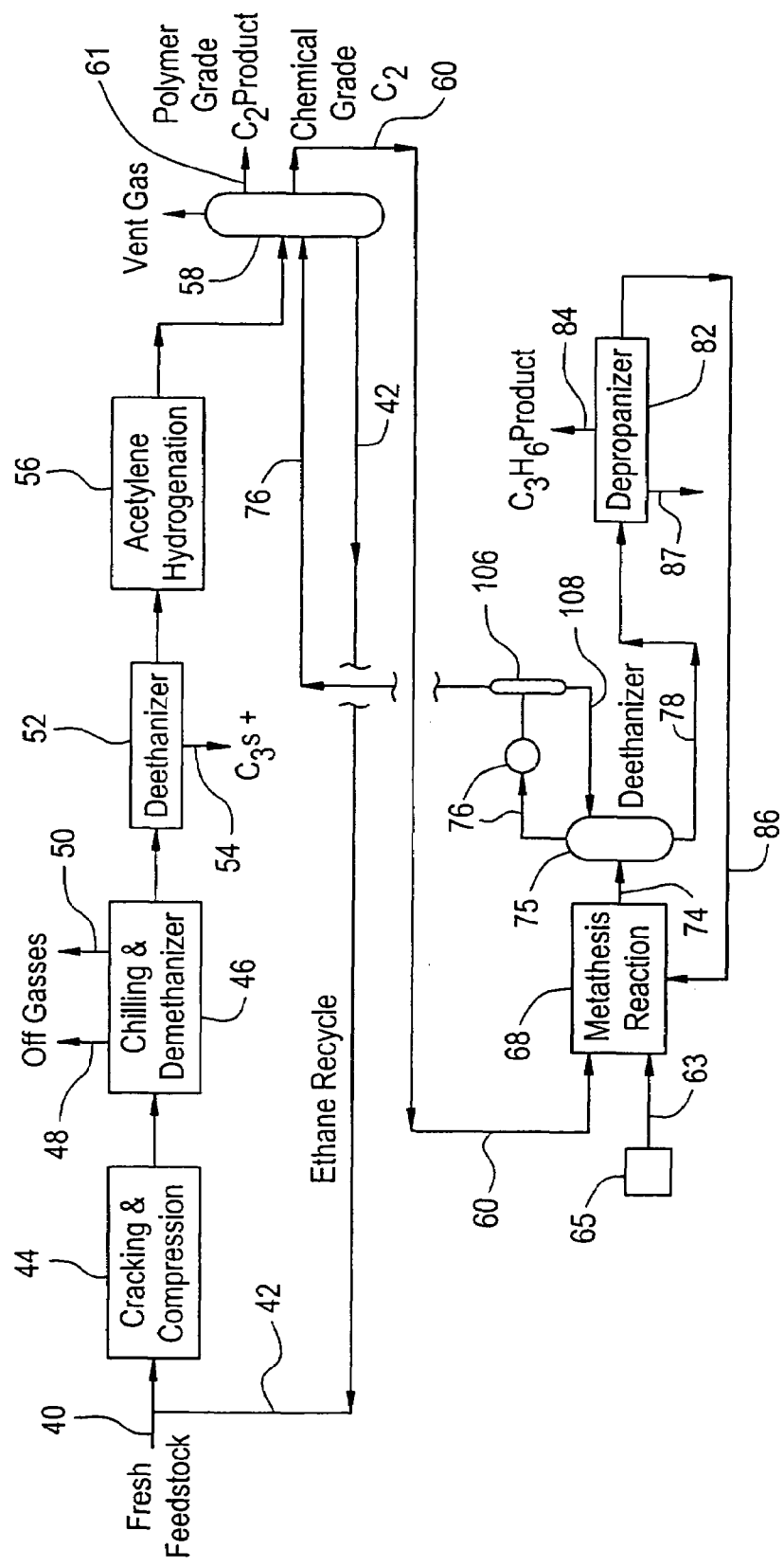
FIG. 5 is a process flow scheme similar to FIG. 3 but eliminating the dimerization section.

FIG. 5 depicts the integration concepts taught in FIG. 3 when utilized in a steam cracker plant with a metathesis section to increase propylene production. The feedstock to the steam cracker can be any hydrocarbon, from ethane to vacuum gas oil. Ethylene fractionator 58 produces a polymer-grade product 61 and a chemical-grade product 60. The chemical grade product flows to the metathesis reaction section 68 along with fresh butene feedstock 63 and a recycle butenes stream 86. The source 65 of the fresh butene stream 63 could be derived from the unsaturated $C_4$'s present in stream 54 and/or potentially other unsaturated $C_4$'s such as refinery off-gas streams or catalytic dehydrogenation streams. Stream 74 exits the metathesis reaction section 68 and is composed of an equilibrium or near equilibrium mixture of propylene, ethylene and butenes along with mostly-paraffin inerts and a small quantity of $C_5$'s and heavier. This stream then flows to the deethanizer and is processed as described for the FIG. 3 configuration. The net overhead 110 is returned back to the ethylene fractionator 58 in the ethylene plant recovery system. No separate recycle of ethylene to the metathesis reaction section 68 is typically practiced as was indicated by stream 70 in FIG. 2. Rather, the metathesis reaction is operated once through in ethylene flow. The deethanizer bottoms 78 flows to the depropanizer 82. Polymer-grade propylene is taken off as stream 84 and, when combined with the propylene recovered from stream 54, would clearly increase the total propylene production in the plant. Recycle $C_4$'s are removed as a side stream 86 near the bottom of the fractionating section of the depropanizer and sent to the metathesis section 68 as previously described. A purge stream 87 is taken from the bottom of the depropanizer to remove $C_5$'s and heavier and to limit butane concentration buildup.

The advantage of the integration concept is a decrease in operating and capital costs for the total plant, as compared to using polymer-grade ethylene as the feed to the metathesis section. It is less capital intensive and more efficient to produce chemical-grade than polymer-grade ethylene. However, with chemical-grade ethylene, ethane concentration can build up in the metathesis section, if recycled directly back from the deethanizer to the metathesis reaction section. This integration enables the use of chemical-grade ethylene while avoiding ethane concentration buildup.

Figure 6:
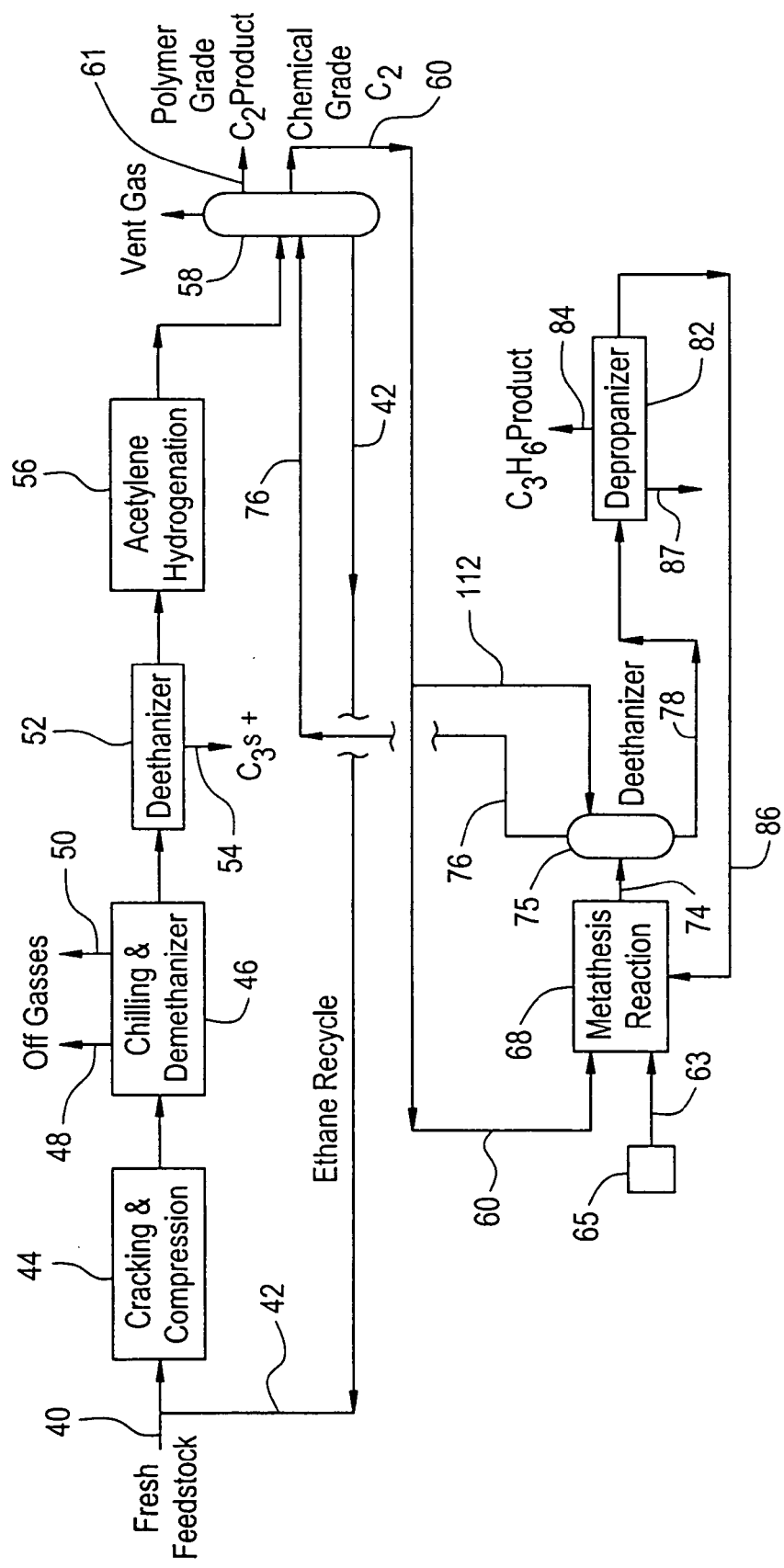
FIG. 6 is a process scheme similar to FIG. 4 but eliminating the dimerization section.

Similarly, FIG. 6 depicts the integration concepts taught in FIG. 4 when utilized in a system with only a metathesis section to increase propylene production. Fresh feed 40 to the cracking section can be any typically utilized steam cracker feedstock from ethane to vacuum gas oil. The processing steps in the ethylene plant recovery section up to the ethylene fractionator are as previously described and generally known to those skilled in the art. The ethylene fractionator 58 produces a chemical-grade ethylene stream 60 which flows to the metathesis reaction section 68. Here again, it is combined with fresh butene feedstock 63 and a recycle butene stream 86. Exiting the metathesis reactor, stream 74 flows to the deethanizer 75, wherein $C_2$'s are taken overhead as stream 76. This stream flows directly to the $C_2$ fractionator 58. The deethanizer has no overhead condenser. Rather, stream 112 taken from the chemical-grade ethylene side draw steam 60 from the $C_2$ fractionator 58 provides reflux to the deethanizer 75. The deethanizer bottom stream, 78, flows to the depropanizer 82, and the subsequent processing is similar to that described for FIG. 5.

The advantage of this process scheme is lower capital and lower operating costs for the total plant as compared to utilizing polymer-grade ethylene to feed the metathesis plant. There is a savings in required equipment items as compared to the FIG. 5 scheme which also utilizes chemical-grade ethylene and the capital cost of this scheme should be lower than for the FIG. 5 scheme.

The invention claimed is:

1. A method of producing propylene from ethane comprising the steps of:
   a. steam cracking an ethane or primarily ethane feedstock thereby producing a cracking product containing ethylene, hydrogen, ethane, methane, acetylene and $C_3$ and heavier hydrocarbons;
   b. treating said cracking product in an ethylene plant recovery section including removing said hydrogen, methane and $C_3$ and heavier hydrocarbons therefrom and converting said acetylene therein primarily to ethylene to thereby produce a treated cracking product containing primarily ethylene and ethane and including fractionating said treated cracking product in a $C_2$ fractionator and obtaining an ethylene fraction of chemical grade ethylene having an ethylene content of less than 99% by volume and a bottoms ethane fraction;
   c. recycling said bottoms ethane fraction to said steam cracking;
   d. reacting by dimerization in a dimerization section a first portion of said ethylene fraction thereby producing a butene-rich stream containing heavier hydrocarbons, ethylene and ethane;
   e. separating said heavier hydrocarbons in a butene separator from said butene-rich stream and feeding the remaining butene-rich stream containing ethylene, ethane and butene to said metathesis section;
   f. reacting by metathesis in said metathesis section the butene in said butene-rich stream with a second portion of said ethylene fraction thereby producing a propylene-rich stream containing propylene, ethylene and ethane;
   g. separating propylene from said ethylene and ethane in said propylene-rich stream, and
   h. recycling at least a first portion of said ethylene and ethane from said propylene-rich stream to said $C_2$ fractionator.

2. A method as recited in claim 1 wherein separation of said propylene from said ethylene and ethane in said propylene-rich stream takes place in a metathesis section deethanizer.

3. A method as recited in claim 2 wherein a second portion of said ethylene and ethane separated from propylene in said metathesis section deethanizer is condensed and returned to said metathesis section deethanizer as reflux.

4. A method as recited in claim 2 wherein all of said ethylene and ethane removed from said propylene-rich stream in said metathesis section deethanizer is recycled directly to said $C_2$ fractionator.

5. A method as recited in claim 4 wherein a third portion of said ethylene fraction from said $C_2$ fractionator is fed to said metathesis section deethanizer as reflux.

6. A method as recited in claim 1 wherein a portion of said ethylene and ethane is removed from said butene-rich stream in a dimerization section deethanizer.

7. A method as recited in claim 6 wherein a first part of said portion of ethylene and ethane removed from said butene-rich stream is recycled to said dimerization section and a second part is purged and recycled to said ethylene plant recovery section.

8. A method as recited in claim 7 wherein said second part of said ethylene and ethane removed from said butene-rich stream is recycled to said $C_2$ fractionator.

9. A method as recited in claim 1 wherein the deethanized propylene-rich stream from metathesis contains butene and other $C_4$ and heavier hydrocarbons and wherein said butene and other $C_4$ and heavier hydrocarbons are separated therefrom and fed to said butene separator in said dimerization section.

10. A method as recited in claim 9 wherein said ethane or primarily ethane feedstock comprises a mixed ethane/propane feedstock containing at least 70% ethane.

11. A method as recited in claim 1 wherein said ethane or primarily ethane feedstock comprises a mixed ethane/propane feedstock containing at least 70% ethane.

12. A method as recited in claim 1 where additional propylene product is obtained from unsaturated $C_3$'s produced in the steam cracker.

13. A method as recited in claim 1 wherein an additional ethylene fraction is obtained in said step of fractionating said treated cracking product and wherein said additional ethylene fraction is a polymer grade ethylene product having an ethylene content greater than 99% by volume.

14. A method as recited in claim 1 wherein said butene for reaction in said metathesis section further comprises butene recovered from said heavier hydrocarbons in said cracking product.

15. A method as recited in claim 1 wherein said butene for reaction in said metathesis section further comprises butene from a source selected from refinery processes and the catalytic dehydrogenation of butanes.

16. A method as recited in claim 1 wherein said ethylene fraction has an ethylene content of 90–95%.

17. A method of producing propylene from ethane comprising the steps of:
   a. steam cracking an ethane or primarily ethane feedstock thereby producing a cracking product containing ethylene, hydrogen, ethane, methane, acetylene and $C_3$ and heavier hydrocarbons;
   b. treating said cracking product in an ethylene plant recovery section including removing said hydrogen, methane and $C_3$ and heavier hydrocarbons therefrom and converting said acetylene therein primarily to ethylene to thereby produce a treated cracking product containing primarily ethylene and ethane and including fractionating said treated cracking product in a $C_2$ fractionator and obtaining a chemical grade ethylene fraction having an ethylene content of less than 99% by volume, a polymer grade ethylene fraction having an ethylene content of at least 99.5% by volume, and a bottoms ethane fraction;
   c. recycling said bottoms ethane fraction to said steam cracking;
   d. reacting by dimerization in a dimerization section a first portion of said chemical grade ethylene fraction thereby producing a butene-rich stream containing heavier hydrocarbons, ethylene and ethane;
   e. separating said heavier hydrocarbons in a butene separator from said butene-rich stream and feeding the remaining butene-rich stream containing ethylene, ethane and butene to said metathesis section;
   f. reacting by metathesis in said metathesis section the butene in said butene-rich stream with a second portion of said chemical grade ethylene fraction thereby producing a propylene-rich stream containing propylene, ethylene and ethane;
   g. separating propylene from said ethylene and ethane in said propylene-rich stream, and
   h. recycling at least a first portion of said ethylene and ethane from said propylene-rich stream to said $C_2$ fractionator.

18. A method as recited in claim 17 wherein separation of said propylene from said ethylene and ethane in said propylene-rich stream takes place in a metathesis section deethanizer.

19. A method as recited in claim 18 wherein a second portion of said ethylene and ethane separated from said propylene-rich stream in said metathesis section deethanizer is condensed and returned to said metathesis section deethanizer as reflux.

20. A method as recited in claim 18 wherein a third portion of said chemical grade ethylene fraction from said $C_2$ fractionator is fed to said metathesis section deethanizer as reflux.

21. A method as recited in claim 18 wherein the deethanized propylene-rich stream from metathesis contains butene and other $C_4$ and heavier hydrocarbons and wherein said butene and other $C_4$ and heavier hydrocarbons are separated therefrom and fed to said butene separator in said dimerization section.

22. A method as recited in claim 18 wherein all of said ethylene and ethane removed from said propylene-rich stream in said metathesis section deethanizer is recycled to said $C_2$ fractionator.

23. A method as recited in claim 17 wherein said chemical grade ethylene fraction has an ethylene content of 90–95%.

24. A method as recited in claim 17 wherein said ethane or primarily ethane feedstock comprises a mixed ethane/propane feedstock containing at least 70% ethane.

25. A method as recited in claim 17 where additional propylene product is obtained from unsaturated $C_3$'s produced in the steam cracker.

* * * * *